(12) United States Patent
Blauw et al.

(10) Patent No.: US 9,134,270 B2
(45) Date of Patent: Sep. 15, 2015

(54) AMORPHOUS THIN FILM FOR SENSING

(75) Inventors: Michiel Blauw, Breda (NL); Van Anh Dam Thi, Eindhoven (NL); Jinesh Kochupurackal, Eindhoven (NL)

(73) Assignee: Stichting IMEC Nederland, Eindhoven (NL)

( * ) Notice: Subject to any disclaimer, the term of this patent is extended or adjusted under 35 U.S.C. 154(b) by 300 days.

(21) Appl. No.: 13/071,405

(22) Filed: Mar. 24, 2011

(65) Prior Publication Data
US 2011/0263036 A1    Oct. 27, 2011

Related U.S. Application Data

(60) Provisional application No. 61/317,586, filed on Mar. 25, 2010.

(51) Int. Cl.
*G01N 27/00* (2006.01)
*G01N 27/414* (2006.01)

(52) U.S. Cl.
CPC ........ *G01N 27/4146* (2013.01); *G01N 27/4148* (2013.01)

(58) Field of Classification Search
None
See application file for complete search history.

(56) References Cited

U.S. PATENT DOCUMENTS 7,816,681 B2 * 10/2010 Moon et al. ............ 257/43
2005/0235735 A1   10/2005 Doll et al.

OTHER PUBLICATIONS

Du, X. et al. Thinckness dependence of sensor response for CO gas sensing by tin oxide films using atomic layer deposition, 2008, SAensors and ACtuators B, vol. 135, pp. 152-160.*
Kandasamy, S. et al. Electrical characterization and hydrogen gas sensing properties of a n-ZnO/p-SiC Pt-gate metal semiconductor field effect transistor, 2007, Applied Physics Letters, vol. 90, pp. 064103 1-064103 3.*
Kim, K-S. et al. A nanopore structured high performance toluene gas sensor made by nanoimprinting method, 2010, Sensors, vol. 10, pp. 765-774.*
Fan, Z. et al., Gate-refreshable Nanowire Chemical Sensors, Applied Physics Letters, vol. 86, 123510 (2005).

* cited by examiner

*Primary Examiner* — Robert Xu
(74) *Attorney, Agent, or Firm* — Knobbe Martens Olson & Bear LLP

(57) ABSTRACT

An apparatus and method for low-power sensing, for example, sensing of chemical or biochemical analytes in a gas or liquid phase are disclosed. One aspect relates to the use of a thin continuous film without grain boundaries as a sensing layer in devices for sensing a predetermined analyte and to low power devices having such sensing layer. The sensing layer has a surface exposed to the analyte. The electrical impedance of the sensing layer changes upon adsorption of the predetermined analyte on the exposed surface of the sensing layer. The sensing layer may have a thickness in the range between about 1 nm and 100 nm, such as between about 1 nm and 30 nm. The sensing layer may be an amorphous layer.

3 Claims, 4 Drawing Sheets

AMORPHOUS THIN FILM FOR SENSING

CROSS-REFERENCE TO RELATED APPLICATIONS

This application claims priority under 35 U.S.C. §119(e) to U.S. Provisional Patent Application 61/317,586 filed on Mar. 25, 2010, which application is hereby incorporated by reference in its entirety.

BACKGROUND OF THE INVENTION

1. Field of the Invention

The present invention relates to thin films that can be used as a sensing layer in a range of sensing devices, applications thereof and a method of manufacturing. More in particular the present invention relates to low-power sensing, for example sensing of chemical and biochemical analytes in a gas phase or liquid phase.

2. Description of the Related Technology

Low-power chemical sensing is an enabler for emerging wireless autonomous transducer applications. These applications include energy scavengers that ensure autonomous operation over extended periods of time. Therefore, low-power circuits are needed because the power generated by energy harvesting from the environment is limited. Besides low-power RF-communication, digital processing and AD-conversion, these applications also include low-power sensors and actuators to interact with the environment.

In addition to the requirement of low-power operation and low operating voltage, the sensors should be sensitive and selective as needed by the targeted applications.

Detection of a specific analyte is often achieved by monitoring a change in the physical properties, for example impedance (conductance, capacitance), dielectric constant, and/or work function of a sensing material. Many different materials are used for sensing, ranging from polymers to inorganic materials such as oxides, nitrides, and semiconductors.

For example, for sensitive and selective detection of gases, metal oxides including semiconducting and insulating materials are often used as gas-sensitive layers in gas sensing devices. These devices need to be heated to well above 100° C., typically up to 400° C. in order to enhance gas adsorption and desorption. Operating the sensing devices at elevated temperatures is also required to enhance gas diffusion into the metal oxide layer. Such is a disadvantage e.g. in terms of power consumption and durability of the material.

In U.S. Pat.No. 2005/0235735 a gas sensor is described wherein the adsorption probability of a gas is controlled by means of an electric field. Such gas sensors can therefore be made subject to electrical modulation of their sensitivity to various gases. An improved selectivity for a target gas may be obtained, and operating temperatures can be reduced to below 200° C. These devices also need to be heated for proper operation.

However, the power consumption for heating is excessive compared to the power budget dictated by wireless, autonomous transducer systems. Thus for low-power applications, there is a need for sensitive and selective sensors that can operate at room temperature or ambient temperature.

Metal oxide nanowires have also been used for gas sensing. The sensitivity of nanowire devices can be high because of their high surface-to-volume ratio. An electric field can influence the surface properties and molecular adsorption in the case of nanowire devices. Certain chemical reactions that have high activation energy can be enhanced or even reversed with an electric field at room temperature or ambient temperature, which is a very important property for low-power gas sensors. The electric field enables both enhancement of gas adsorption (sensing) and desorption (refreshing) in the device by modulating the surface states of the sensing materials. This implies that the electric field can be a substitute for temperature both in sensing and refreshing the nanowire sensors. Moreover, the adsorption of a particular kind of molecules is characterized by a certain activation energy, which can be reduced by application of an electric field, improving the selectivity of the device.

For example, it has been reported by Z. Fan et al in "Gate-refreshable nanowire chemical sensors", Appl. Phys. Lett. 86, 123510 (2005), that devices comprising 60 nm ZnO nanowires on top of a 500 nm thick gate oxide layer require a gate voltage of 60 V to refresh after exposure to 10 ppm $NO_2$. In this case, the required electric field is approximately 1.2 $MV \cdot cm^{-1}$. Lower voltages that are within the requirements of autonomous systems can be achieved by using thinner gate oxides.

However, the integration of nanowires in a semiconductor fabrication process is complicated if not impossible due to thermal constraints during the growth of nanowires and due to problems related to the positioning of individual nanowires on a chip.

SUMMARY OF CERTAIN INVENTIVE ASPECTS

In a first aspect the present invention relates to low power devices for sensing a predetermined analyte, the devices comprising a sensing layer having a surface in use exposed to the analyte, wherein the electrical impedance of the sensing layer changes upon adsorption of the predetermined analyte on the exposed surface of the sensing layer, and wherein the sensing layer is a thin continuous film without grain boundaries. The sensing layer preferably has a thickness in the range between about 1 nm and 100 nm, such as between about 1 nm and 30 nm. The sensing layer can be an amorphous layer or a single crystalline layer. It can be a dielectric layer or a semiconducting layer.

The sensing layer can for example be formed of one or more of a polymer, an inorganic material, such as an oxide, a nitride, and a semiconductor, such as $SiO_2$, $Al_2O_3$, $HfO_2$, $Ta_2O_5$, $ZrO_2$, titanium oxide, iron oxide, manganese oxide, chromium oxide, cobalt oxide, nickel oxide, copper oxide, zinc oxide, tin oxide, molybdenum oxide, zirconium oxide, tungsten oxide, iridium oxide, an oxide of the lanthanide series, a noble metal catalyst particle, SiN, SiC, n-type or p-type doped silicon, a III-V binary, ternary and quaternary alloy, such as GaN, and a II-VI compound.

The device may comprise at least one first measurement electrode and at least one second measurement electrode adapted for measuring the electrical impedance of the sensing layer, thereby sensing the predetermined analyte based on detecting changes of the electrical impedance.

The device can further comprise at least one field electrode adapted for applying an electric field over the sensing layer, thereby electrically controlling adsorption and/or desorption of the predetermined analyte at the exposed surface of the sensing layer.

One of the first measurement electrode and the second measurement electrode can be used as a field electrode adapted for applying an electric field over the sensing layer, thereby electrically controlling adsorption and desorption of the predetermined analyte at the exposed surface of the sensing layer.

The device can for example be a capacitor wherein the sensing layer is an electrically insulating layer being provided between the first measurement electrode and the second measurement electrode.

The device can for example be a transistor wherein the sensing layer is a gate dielectric layer, wherein the first measurement electrode is a source electrode, wherein the second measurement electrode is a drain electrode and wherein the field electrode is the gate electrode.

The device can for example be a transistor wherein the sensing layer is a semiconducting channel layer, wherein the first measurement electrode is a source electrode, wherein the second measurement electrode is a drain electrode and wherein the field electrode is the gate electrode.

The sensing layer can be provided on a structured surface comprising nanoscopic and/or microscopic structures such as lines, dots, trenches or pores preferably having an aspect ratio suited to facilitate easy access for the analyte, a complex 3D structure, such as one having an increased effective surface area, an open structure to allow easy molecule penetration through it, such as a pyramid or an array of pyramid-like structures, a periodic array of structures, and a sharp edge, preferably periodically appearing.

In a second aspect the present invention relates to the use of a thin continuous film without grain boundaries as a sensing layer in a device for sensing a predetermined analyte, the sensing layer having a thickness in the range between about 1 nm and 100 nm, such as between about 1 nm and 30 nm. The sensing layer can be an amorphous layer or a single crystalline layer. It can be a dielectric layer or a semiconducting layer. Sensing can be performed at ambient temperature.

The sensing layer can for example be formed of one or more of a polymer, an inorganic material, such as an oxide, a nitride, and a semiconductor, such as $SiO_2$, $Al_2O_3$, $HfO_2$, $Ta_2O_5$, $ZrO_2$, titanium oxide, iron oxide, manganese oxide, chromium oxide, cobalt oxide, nickel oxide, copper oxide, zinc oxide, tin oxide, molybdenum oxide, zirconium oxide, tungsten oxide, iridium oxide, an oxide of the lanthanide series, a noble metal catalyst particle, SiN, SiC, n-type or p-type doped silicon, a III-V binary, ternary and quaternary alloy, such as GaN, and a II-VI compound.

One inventive aspect relates to a semiconductor apparatus, such as a CMOS apparatus comprising a device for sensing a predetermined analyte as described above.

One inventive aspect relates to thin films that can be used as sensing films in a range of sensing devices that have low power consumption, good selectivity, good sensitivity and a fast response, wherein the sensing devices can operate at room temperature or ambient temperature and wherein the sensing devices can be made with standard semiconductor fabrication techniques. In certain embodiments the thin sensing films are continuous, ultra thin films without grain boundaries, for example amorphous films. Sensing refers to sensing of atoms, molecules and/or ions, such as for example chemical and/or biochemical analytes, in the gas phase or in the liquid phase.

One inventive aspect relates to thin films that can be used as a sensing layer in sensing devices, and sensing devices comprising such thin films, wherein the thin films are continuous ultrathin films without grain boundaries. In certain embodiments the sensing films are e.g. amorphous films with a thickness in the range between about 1 nm and 100 nm, e.g. in the range between about 1 nm and 30 nm. Using such thin films may result in a high sensitivity, a fast response, low operational voltages and the possibility of using electric fields for controlling adsorption and desorption, thus allowing operation at room temperature or ambient temperature.

A sensing device for sensing a predetermined analyte according to one inventive aspect comprises a sensing layer wherein the electrical impedance of the sensing layer changes upon adsorption of the predetermined analyte on an exposed surface of the sensing layer, and wherein the sensing layer is a thin continuous film without grain boundaries. In preferred embodiments the sensing layer is an amorphous film with a thickness in the range between about 1 nm and 100 nm, e.g. in the range between about 1 nm and 30 nm. The exposed surface of the sensing layer is a surface exposed to a local environment, e.g. a liquid or a gas comprising the predetermined analyte to be sensed.

In an example the sensing device may further comprise a first measurement electrode and a second measurement electrode for measuring the electrical impedance of the sensing layer, thereby sensing the predetermined analyte based on detecting changes of the electrical impedance of the sensing layer. Measuring the electrical impedance can for example comprise measuring the electrical conductance or it can comprise measuring the electrical capacitance. The first measurement electrode and the second measurement electrode can be provided at a same side of the sensing layer, or the first measurement electrode and the second measurement electrode can be provided at opposite sides of the sensing layer.

In an example the sensing device may further comprise at least one field electrode for applying an electric field over the sensing layer, thereby electrically controlling adsorption and/or desorption of the predetermined analyte at the exposed surface of the sensing layer. Electrically controlling adsorption can be used for improving the sensitivity and/or the selectivity of the sensing device. Electrically controlling desorption can be used for resetting or regenerating the device, thereby avoiding the need for heating the device. The electric field can for example be applied by providing a voltage pulse at least one field electrode.

In certain embodiments one of the first and the second measurement electrode can be used as a field electrode.

The sensing device can for example comprise a capacitor structure wherein the sensing layer is an electrically insulating layer being provided between the first measurement electrode and the second measurement electrode.

The sensing device can for example comprise a transistor structure wherein the sensing layer is a gate dielectric layer or wherein the sensing layer is a semiconducting channel layer. In such embodiments the field electrode can function as a gate electrode, the first measurement electrode can for example function as a source electrode and the second measurement electrode can for example function as a drain electrode.

For purposes of illustrating certain inventive aspects and the advantages achieved over the prior art, certain objects and advantages have been described herein above. Of course, it is to be understood that not necessarily all such objects or advantages may be achieved in accordance with any particular embodiment of the invention. Thus, for example those skilled in the art will recognize that the invention may be embodied or carried out in a manner that achieves or optimizes one advantage or group of advantages as taught herein without necessarily achieving other objects or advantages as may be taught or suggested herein. Further, it is understood that this summary is merely an example and is not intended to limit the scope of the invention. The invention, both as to organization and method of operation, together with features and advantages thereof, may best be understood by reference to the following detailed description when read in conjunction with the accompanying drawings.

DETAILED DESCRIPTION OF CERTAIN ILLUSTRATIVE EMBODIMENTS

Figure 1:
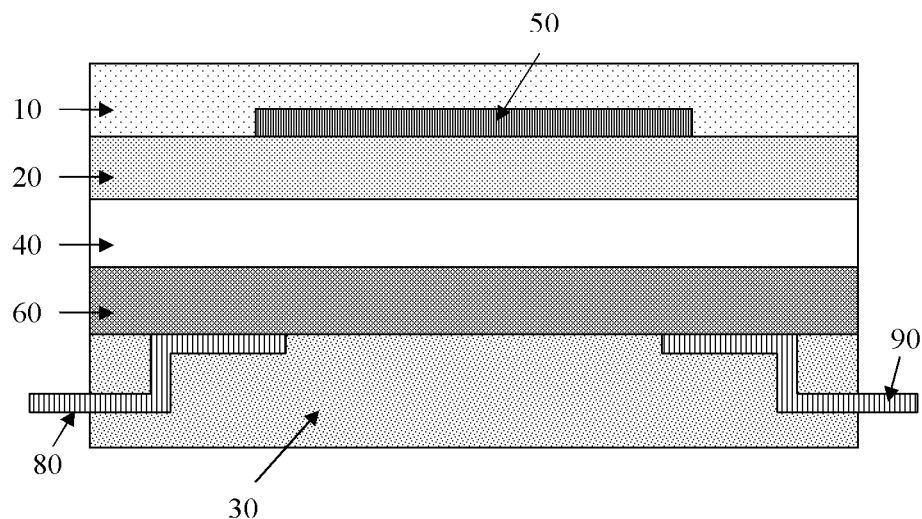
FIG. 1 shows a schematic layout of an exemplary structure for sensing of analytes using an amorphous thin film in accordance with one embodiment.

In the following detailed description, numerous specific details are set forth in order to provide a thorough understanding of the invention and how it may be practiced in particular embodiments. However, it will be understood that the present invention may be practiced without these specific details. In other instances, well-known methods, procedures and techniques have not been described in detail, so as not to obscure the present invention. While the present invention will be described with respect to particular embodiments and with reference to certain drawings, the invention is not limited hereto. The drawings included and described herein are schematic and are not limiting the scope of the invention. It is also noted that in the drawings, the size of some elements may be exaggerated and, therefore, not drawn to scale for illustrative purposes.

Furthermore, the terms first, second, third and the like in the description, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, bottom, over, under and the like in the description are used for descriptive purposes and not necessarily for describing relative positions. It is to be understood that the terms so used are interchangeable under appropriate circumstances and that the embodiments of the invention described herein are capable of operation in other orientations than described or illustrated herein.

The terms "film" and "layer" both relate to a relatively thin 2-dimensional homogeneous structure.

It is to be noticed that the term "comprising" should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B.

Certain embodiments relate to thin films that can be used as sensing films or sensing layers in a range of sensing devices that have low power consumption, good selectivity, good sensitivity and a fast response, wherein the sensing devices can operate at room temperature or ambient temperature and wherein the sensing devices can be made with standard semiconductor fabrication techniques. In one embodiment, thin sensing films are continuous, ultrathin films without grain boundaries. The thickness of these sensing films may be in the range between about 1 nm and 100 nm. For example, sensing devices in one embodiment can advantageously be used for sensing chemical and/or biochemical analytes in the gas phase or in the liquid phase.

Thin sensing films according to one embodiment are continuous, ultra thin films without grain boundaries that can be used in a range of sensing devices. In a sensing device, the thin sensing film according to one embodiment is exposed to a local environment comprising an analyte to be detected. The local environment can be a gas or a liquid that may contain atoms, molecules or ions to be detected, such as for example chemical or biochemical analytes. A sensing device according to one embodiment further comprises at least two measurement electrodes for sensing a predetermined analyte, based on impedance measurements, for example conductance measurements or capacitance measurements. Conductance measurements can comprise detecting changes in charge carrier density in the sensing film. Capacitance measurements can comprise measuring the capacitance between two electrodes with a sensing film in between. In case of sensing based on conductivity measurements, four measurement electrodes can be used in order to eliminate the contact resistance. A sensing device according to one embodiment further comprises a field electrode, wherein the field electrode is in contact with a dielectric layer. The field electrode can be used for applying an electric field for electrically controlling adsorption and/or desorption at the exposed surface of the sensing film. The field electrode can also be used for applying an electric field for improving the selectivity of the sensing device. In certain embodiments, one of the measurement electrodes can be used as a field electrode or a separate field electrode can be provided in addition to the measurement electrodes.

It is an advantage of using a continuous film without grain boundaries as a sensing layer that the electric properties are only determined by the bulk material and the outer surface. No grain boundaries exist in these films so that the bulk electric properties have a predominant effect on the impedance measurements. In the case of a semiconducting sensing film, the conductivity of the sensing film (or sensing layer) is proportional to the charge carrier density in the sensing film, which changes according to the amount of adsorbed molecules on its surface. Grain boundaries would form electrostatic barriers, leading to a conductivity that is not proportional to the charge carrier density. Moreover, the diffusion of molecules in and out of a film is strongly influenced by grain boundaries. Therefore, the absence of grain boundaries leads to a conductivity that is proportional to the charge carrier density such that there is a direct relation between adsorption and conductance. This makes interpretation of the sensor output more straightforward. For capacitance measurements the use of amorphous films is also beneficial, for example because the amount of pinholes can be reduced and thus the electric breakdown voltage can be higher as compared to films comprising grain boundaries.

It is an advantage of using ultra thin sensing films with nanoscale thickness that it allows obtaining a similar (or even better) surface to volume ratio as in the case of nanowires, resulting in a good performance, more in particular a high sensitivity and a fast response. Ultra thin films allow a fast diffusion of analytes through the entire thickness of the sensing layer. In addition, they allow low operational voltages. For example, in embodiments wherein the sensing film forms the channel of a TFT (thin film transistor) structure, the thinner the sensing film, the lower the amount of charge carriers in the channel per unit area, and thus the lower the electric field needed for refreshing the sensor. For capacitive sensors, e.g. sensors having a MIS (metal insulator semiconductor) structure or a MIM (metal insulator metal) structure, the thinner the sensing film, the lower the operational voltage needed to generate an electric field large enough to refresh the device.

Ultra thin films without grain boundaries can be single crystalline films or amorphous films. In certain embodiments, amorphous films are used, because it is very difficult to form large area single crystalline thin films, especially at low temperatures. In certain embodiments the thin sensing films are formed by means of ALD (atomic layer deposition).

In certain embodiments both insulating and semiconducting sensing materials can be used for forming the thin sensing films. Examples of sensing materials that can be used are $SiO_2$, $Al_2O_3$, $HfO_2$, $Ta_2O_5$, $ZrO_2$, titanium oxides, iron oxides, manganese oxides, chromium oxides, cobalt oxides, nickel oxides, copper oxides, zinc oxides, tin oxides, molybdenum oxides, zirconium oxides, tungsten oxides, iridium oxides, oxides of lanthanide series, mixtures of these oxides, and mixtures of these oxides with noble metal catalyst particles. Beside oxides, the sensing materials can comprise nitrides (e.g. SiN) and/or carbides (e.g. SiC). Insulating sensing materials can be used for sensing based on capacitance measurements. Semiconducting sensing materials can be used for sensing based on conductance measurements. Semiconductors such as for example II-VI compounds and III-V compounds including nitrides such as GaN can also be used for sensing based on conductance measurements.

It is an advantage of using continuous ultra thin sensing films without grain boundaries according to one embodiment that it allows obtaining sensing devices that operate strictly at room temperature or ambient temperature, i.e. it allows obtaining sensing devices wherein the need for heating is avoided (both for sensing and refreshing). Because of the nanoscale thickness of the sensing layer, electric fields can be used to control adsorption and desorption, thereby avoiding the need for heating the devices. Operation at room temperature or ambient temperature has several advantages. First, it reduces the power consumption because no heating of the sensing material is needed, which makes it more attractive for portable and embedded applications. Second, it facilitates the integration of the sensing device or sensing structure with (e.g. on top of) low-power CMOS-based driver circuitry that operates at (or only slightly above) room temperature or ambient temperature. This ensures that the morphology of the thin sensing film remains unaffected, which helps to enable stable and reproducible sensing. The stability of the sensing material is a prerequisite for reproducible sensing and implies that the sensing structure operates at room temperature or at a sufficiently low temperature to avoid irreversible morphological changes such as phase changes. The sensing device may operate at a temperature lower than about 100° C., particularly at a temperature in the range between about −40° C. and 50° C., e.g. between about 0° C. and 50° C. more particularly at room temperature or ambient temperature such that the need for heating the device is avoided.

The desorption of molecules or ions may become limited at room temperature or ambient temperature, which eventually leads to a saturated sensing film surface making further measurements impossible. However, an applied electric field (e.g. by means of a field electrode) can result in desorption of ionosorbed molecules at room temperature or ambient temperature. Therefore, the thin sensing films in one embodiment may be regenerated (surface regeneration after adsorption of molecules) by means of the electro adsorptive effect, i.e. by providing an electrical field influencing the adsorption of molecules on the surface of the sensing layer, leading to desorption of molecules. Regeneration can be obtained by applying an electric field, for example by applying a voltage pulse to a field electrode, the pulse parameters depending on the device geometry and on the type of material. It is an advantage of being able to regenerate the surface of the thin sensing film based on the electro adsorptive effect that it allows operation at room temperature or ambient temperature. However, preferably hysteresis effects that are due to polarization are avoided.

Certain embodiments relate to using a continuous ultra thin sensing film, e.g. an amorphous film, in sensing devices, wherein the sensing devices can be reset and calibrated by exposure to an electric field, e.g. applied by a field electrode. An electric field can enhance the adsorption of molecules on a sensing film surface. As a result, the sensitivity can increase using an electric field. Furthermore, an electric field can also increase the selectivity because the electric field at the onset of adsorption is different for each molecular analyte. An electric field can for example be applied by a field electrode. It can enhance adsorption (for enhanced sensitivity) and it can lead to desorption of molecules (for regeneration) on sensing layer surfaces at room temperature or ambient temperature, depending on the polarity of the applied electric field.

The thickness of the thin sensing film, e.g. amorphous sensing film, is in the range from a few nanometers to a few tens of nanometers. Films with a nanoscale film thickness have several advantageous properties for sensing. The surface-to-volume ratio obtained for such a thin film is comparable to the surface-to-volume ratio of a nanowire but, as opposed to nanowires, the thin film can be formed by using standard semiconductor fabrication techniques. The response of a film with a nanoscale thickness is faster as compared to the response of a thicker film because of the shorter diffusion length. The relatively thick films that are often used in prior art solutions slow down the response significantly. Ideally, an instantaneous response is obtained following variations of the analyte concentrations. However, the adsorption and desorption kinetics also set a timescale on the response.

When using a semiconducting thin film as a sensing film, for example in embodiments wherein the sensing film forms the channel of a TFT device on top of a back gate, the entire sensing film needs to be depleted from charge carriers before the initial state (i.e. the state without adsorbed molecules) of the sensing layer surface can be reached. In embodiments as for example illustrated in FIG. 6, wherein a semiconducting sensing film 40 is used, being exposed at a first side to the local environment 30 comprising an analyte to be detected, and at a second side (opposite to the first side) being separated from a field electrode 50 (e.g. used for regeneration of the sensing device) by an insulating film 20, the charge carriers in the sensing film 40 are depleted first at the side of the field electrode 50, i.e. at the second side of the sensing film. Only when the electric field provided by the field electrode is sufficiently strong, charge carriers are depleted from the first side of the sensing film, in the end leading to desorption of molecules from the surface (first side) of the sensing film exposed to the local environment 30. The dielectric medium 20 in between the field electrode 50 and the thin sensing film 40 is characterized by a breakdown field. The larger the amount of charge carriers that needs to be depleted in the sensing film, the higher the electric field needs to be. A sensing film with a nanoscale thickness in accordance with one embodiment limits the amount of charge carriers that needs to be depleted so that the electric field can be kept well below the breakdown field of the dielectric medium, and the operating voltage can be kept low.

Figure 6:
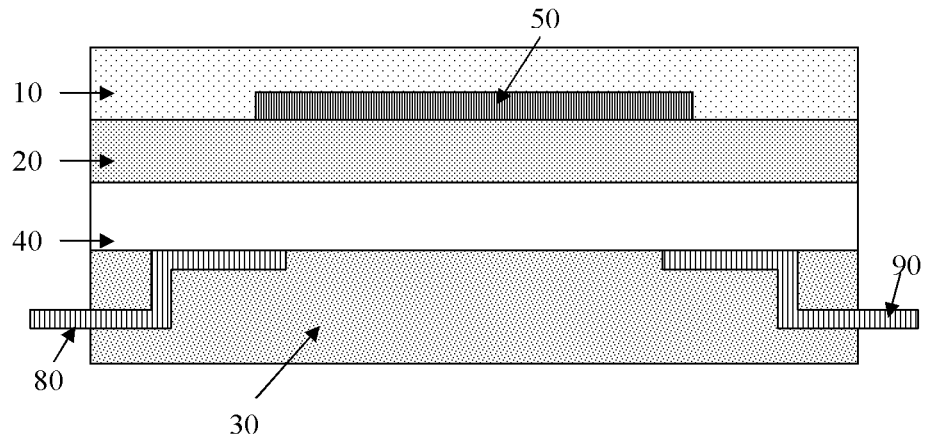
FIG. 6 shows a sensing device having a TFT structure with a sensing layer having the function of transistor channel.

As illustrated in FIG. 6, the field electrode and the thin semiconducting sensing film can be separated by a dielectric medium. However, the field electrode 50 and the semiconducting sensing film 40 can also be separated by a gap. When using such a device for sensing, the gap is exposed to the local environment, i.e. a gas or a liquid comprising an analyte to be detected. In this case, the exposed surface of the sensing film 40 is oriented towards the field electrode 50 and the electric field provided by the field electrode directly acts on the surface where the molecules are adsorbed, such that there is no need for entirely depleting the sensing film to reset the sensing device.

Sensing devices according to one embodiment may be made using state-of-the-art semiconductor fabrication processes such as thin film deposition and lithographic patterning techniques. Using state-of-the-art semiconductor fabrication techniques, it is possible to integrate sensing structures and CMOS electronics on a single wafer (system on chip: SoC) in the back-end-of-line or at wafer level package. The sensing structures and the CMOS electronics can be fabricated in separate clean rooms if the sensing material is a contamination source for CMOS-electronics, because the sensor fabrication is typically the last step of the total fabrication process. Alternatively, it is possible to fabricate the sensing structure on a separate wafer and to bond it to CMOS electronics using chip/wafer bonding and 3D-integration techniques (system in package: SiP). The sensing structures according to one embodiment, which operate at room temperature or ambient temperature, are particularly suited for integration with low-power CMOS circuits, which generate little heat. In certain embodiments the thin sensing films can be formed with low-temperature deposition techniques that are common in existing semiconductor fabrication processes. For example, amorphous, thin sensing films can be obtained by low-temperature deposition techniques, such as (e.g. plasma-enhanced) chemical vapor deposition (CVD), sputter deposition and (e.g. plasma-enhanced) atomic layer deposition (ALD). Dielectric films that can be used for separating the amorphous thin sensing film from the field electrode can also be deposited using CVD or ALD. Moreover, CVD and ALD are standard semiconductor fabrication techniques. ALD is particularly suited for deposition of continuous, uniform films with a nanoscale thickness because of the very good thickness control as a result of the alternating, self-limiting surface reactions of the precursors. Nanoscale control of the film thickness is obtained naturally by pulsing and purging of two different precursor gases that react on the substrate surface in a self-limiting way. ALD is also beneficial for the controllable growth of a stack of layers with nanometer precision. Moreover, using plasma-enhanced processes and processes with other radical sources such as ozone, it is possible to manipulate the defect and charge carrier density and to lower the deposition temperature even further.

In certain embodiments pre-patterned substrates can be used to increase the effective area of a sensing device and to enhance sensing and resetting processes. Nano/microscopic structures such as for example lines or dots can be created on substrates, on which a thin sensing layer in accordance with one embodiment is then provided. Such structures can be formed in silicon by selective etching.

Figure 8:
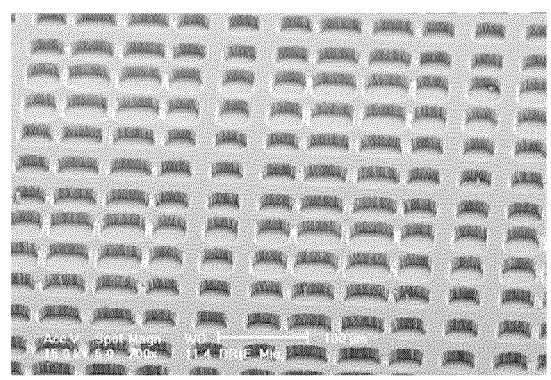
FIG. 8 shows structures etched in silicon that can be used to enhance sensing and resetting processes of sensing devices.

For example, trenches and pores of different shapes and dimensions can be etched in silicon. The aspect ratios of such structures are preferably selected to facilitate easy access for the analyte. From simple structures on silicon to more complex 3D structures can be fabricated. An example of such a structured substrate is shown in FIG. 8. It is an advantage of 3D structures etched in the substrate that they create a very large effective surface area, and the open structures allow easy molecule penetration through it. As a result, the sensitivity of the device increases for a given footprint area. ALD can be used to coat sensing layers according to one embodiment uniformly over these 3D surfaces.

Figure 9:
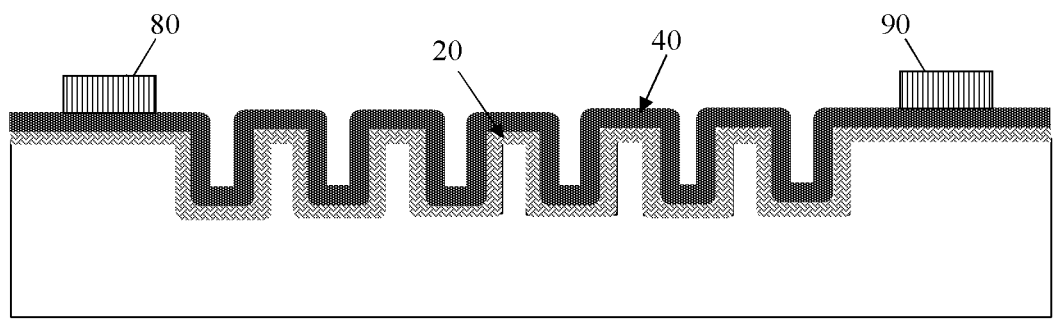
FIG. 9 schematically shows a sensing device with a structured substrate, resulting in an enhanced effective sensing area.

For example, an array of pyramid-like structures can be chemically etched on the silicon surface by preferential etching of the (100) planes over (111) planes. Etching a periodic array of such structures can enhance the effective area for a given footprint area of a sensor. An example of a sensor having an enhanced effective area is schematically illustrated in FIG. 9. It is an advantage of using such pre-structured substrates that the sharp edges periodically appearing on the surfaces generate an enhanced electric field, which can be beneficial for resetting of the devices. The current can flow either perpendicular or parallel to the edges of the structured substrate, depending on the electrodes configuration.

A schematic drawing of a sensing device comprising a sensing layer in accordance with one embodiment is shown in FIG. 1. FIG. 1 shows a general sensing structure, from which elements (e.g. layers, electrodes) can be omitted or other elements can be added in specific embodiments. In the general structure shown in FIG. 1, the sensing device comprises a thin sensing film 40 in accordance with one embodiment. The sensing device further comprises a field electrode 50 that can be separated from the thin sensing layer 40 by a first medium 20, wherein the first medium 20 can for example be a film or wherein the first medium 20 can for example be the local environment, e.g. a gas or liquid comprising an analyte to be detected. In certain embodiments wherein the sensing layer 40 is a semiconducting layer, first medium 20 is an insulating medium. In certain embodiments wherein the sensing layer 40 is an insulating layer, first medium 20 can be omitted. The structure shown in FIG. 1 comprises a semiconducting layer 60 adjacent to the sensing layer 40, at a side opposite to the side where the first medium 20 is present. As will be further illustrated, the semiconducting layer 60 is optional and can be omitted in some specific embodiments. The sensing structure can further comprise a second medium 10 adjacent to the field electrode 50 and/or a third medium 30 at a side of the device opposite to the side of the second medium 10. The second medium 10 and the third medium 30 are preferably dielectric media, such as for example a dielectric substrate or a dielectric support or the local environment, e.g. a gas or a liquid comprising an analyte to be detected. In certain embodiments, at least one of the first medium 20, the second medium 10 and the third medium 30 is the local environment comprising an analyte to be detected. A surface of the sensing layer 40 is exposed to the local environment. The sensing device further comprises at least two measurement electrodes 80, 90. In the general structure shown in FIG. 1, both measurement electrodes 80, 90 are in contact with the semiconducting layer 60. However, e.g. in embodiments where no such semiconducting layer 60 is present, the measurement electrodes may be in contact with another layer, such as for example the thin sensing film 40. In another embodiment, the number of measurement electrodes can be different and/or a measurement electrode can also be used as a field electrode.

The electric properties (impedance of the sensing layer 40) that change as a result of adsorption at a surface of the sensing layer 40 exposed to the local environment are measured with impedimetric techniques. Adsorption at the exposed surface of the sensing layer 40 can be influenced by electric fields, which can enhance the sensitivity and/or selectivity, and which can be used to reset the thin film to its initial state. For this purpose, a field electrode 50 is provided in the direct vicinity of the thin sensing layer 40. The field electrode 50 can be separated from the sensing layer 40 by first dielectric medium 20, especially in embodiments wherein the sensing layer 40 is a semiconducting layer. In embodiments wherein the sensing layer 40 is an electrically insulating layer, the field electrode 50 can be in direct contact with the sensing layer 40. In the exemplary structure shown in FIG. 1, the sensing device comprises one field electrode 50. However, sensing devices according to one embodiment can comprise more than one field electrode.

The measurement electrodes and the field electrodes can take several physical forms and can have different functions in the sensing device, such as capacitor electrodes, source/drain electrodes, gate electrodes (metal top gate, porous top gate, back gate), depending on the structure that incorporates the sensing film 40. The measurement electrodes are provided for measuring changes in the electrical impedance (conductance, capacitance) of the sensing layer 40, whereas the field electrode is provided for creating an electrical field in the sensing layer. For example, the measurement electrodes can be source and drain electrodes of a sensing device having a transistor structure and/or the field electrode can be a gate electrode of a sensing device having a transistor structure. In case of capacitance measurements the function of the measurement electrodes and field electrodes is combined, i.e. one of the measurement electrodes is used as a field electrode, such as for example in a sensing device having a MIS (metal insulator semiconductor) structure (illustrated in FIG. 2) or a MIM (metal insulator metal) structure (illustrated in FIG. 3). Other sensing structures that may comprise a thin sensing film 40 according to one embodiment are for example a FET (field effect transistor) with a gate dielectric sensing layer (FIG. 4), a FET with a gap between the field electrode and the gate dielectric sensing layer (FIG. 5), a TFT (thin film transistor) with sensing channel and back gate (FIG. 6), a TFT with top gate and a gap in between the gate and a sensing channel (FIG. 6). However, the present invention is not limited hereto. Any other suitable sensing structure or sensing device known by a person skilled in the art may comprise a continuous, ultrathin sensing layer without grain boundaries according to one embodiment.

In the case wherein the thin sensing film forms a semiconducting channel in a TFT structure, the sensing material is the active material combining the function of sensing layer and transistor channel, which gives the most direct conversion from adsorption to current. In other device structures the thin sensing film forms a passive material that changes its impedance after exposure to an analyte.

Figure 2:
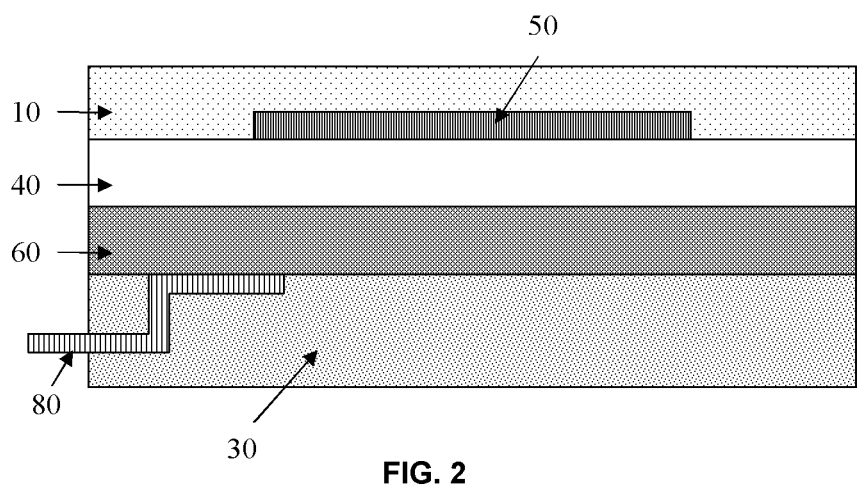
FIG. 2 shows a sensing device having a MIS structure.

FIG. 2 shows an embodiment of a sensing device comprising a thin sensing film 40, wherein the sensing device has a MIS structure. The sensing film 40 (insulator) is at a first side in contact with second medium 10, being the local environment, and at a second side with a semiconducting layer 60 (such as for example n-type or p-type doped silicon or III-V binary, ternary or quaternary alloys). It comprises a measurement electrode 80 and a field electrode 50, the field electrode 50 also being used as a measurement electrode in the configuration shown. Upon adsorption of a molecule at the first side of the sensing film 40, the adsorbed molecules may diffuse from the surface to the bulk of the sensing film 40 and may change the physical properties (such as for example work function, dielectric constant, fixed charge density, mobile charge density) of the bulk of the sensing film 40. The changes of physical properties can be measured using impedimetric techniques. The third medium 30 can be a dielectric medium, e.g. a dielectric substrate or the local environment. Regeneration of the device can be obtained by applying a voltage pulse to the field electrode 50.

Figure 7A:
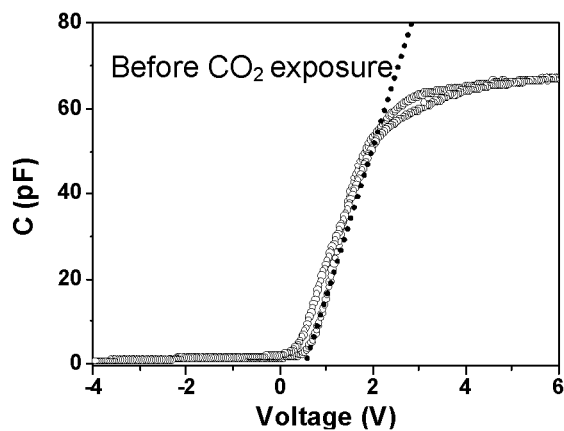
FIG. 7 shows measured results of room temperature $CO_2$ detection using capacitive-voltage measurements of a MIS device with an atomic-layer-deposited metal oxide dielectric sensing layer according to one embodiment.
Figure 7B:
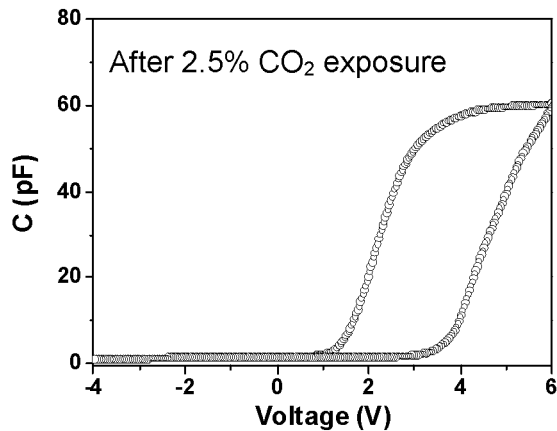

FIG. 7 shows the results of gas measurements performed with a MIS structure as shown in FIG. 2. The capacitance-voltage (C-V) curves of a device in the MIS configuration having an amorphous, thin sensing film deposited by ALD were analyzed. The MIS (metal-insulator-semiconductor) device comprises a 14 nm thick $La_2O_3$ layer (dielectric sensing film 40) deposited on p-type silicon (semiconductor layer 60) using ALD. Al was deposited to form electrodes 50, 80. When exposed to $CO_2$, several parameters of this device change, such as the saturation capacitance, the flat-band voltage and the hysteresis of the CV curves. These parameters give information about the amount of charges generated within the dielectric sensing layer, which is proportional to the amount of gas the device is exposed to. Thus, with a MIS structure it is possible to measure $CO_2$ concentrations accurately and reversibly.

Figure 3:
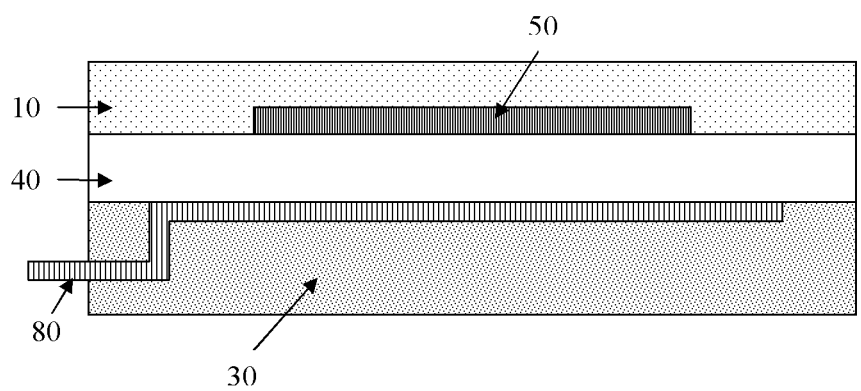
FIG. 3 shows a sensing device having a MIM structure.

FIG. 3 shows an embodiment of a sensing device comprising a thin sensing film 40, wherein the sensing device has a MIM capacitor structure. The sensing film 40 (insulator) is at a first side in contact with third medium 30, being the local environment. A first impedance measurement electrode 80 is provided at the first side of the thin sensing film 40. At a second side of the sensing film 40 opposite to the first side, a field electrode 50 is provided, the field electrode also having the function of an impedance measurement electrode. Upon adsorption of molecules at the first side of the sensing film 40, the adsorbed molecules may diffuse from the surface to the bulk of the sensing film 40 and may change the physical properties (such as work function, dielectric constant, fixed charge density, mobile charge density) of the bulk. The changes of physical properties can be measured using impedimetric techniques, for example using capacitance-voltage measurements. The second medium 10 can be a dielectric medium, e.g. a dielectric substrate. Regeneration of the device can be obtained by applying a voltage pulse to the field electrode 50.

Figure 4:
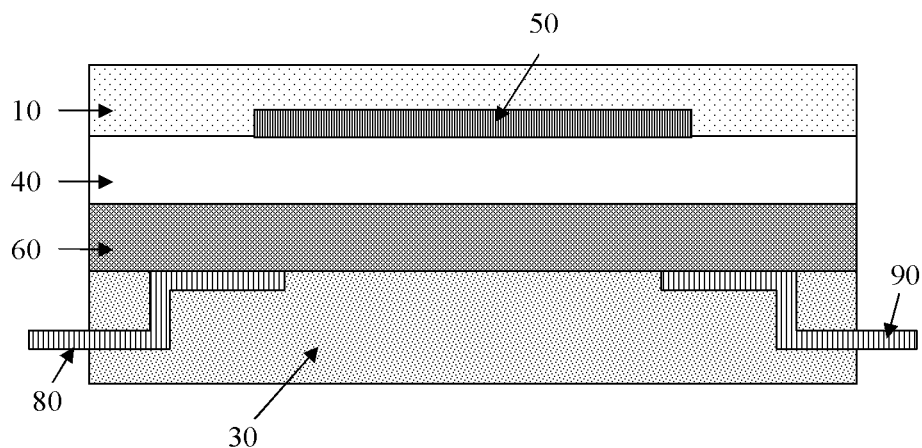
FIG. 4 shows a sensing device having a FET structure with a sensing layer having the function of a gate dielectric layer.

FIG. 4 shows an embodiment of a sensing device comprising a thin sensing film 40, wherein the sensing device has a FET structure and wherein the sensing film 40 (insulating) forms the gate dielectric layer of the FET. In this embodiment, the sensing film 40 is at a first side in contact with second medium 10, being the local environment. The field electrode 50 is the gate electrode of the FET, the thin sensing film 40 is the gate dielectric, provided on a semiconductor layer 60 (such as for example n-type or p-type doped silicon or III-V binary, ternary or quaternary alloys). Third medium 30 can for example be a dielectric medium such as a dielectric substrate or the local environment. The device comprises a first measurement electrode 80 and a second measurement electrode 90 in contact with the semiconductor layer 60, the electrodes having the function of a source electrode and a drain electrode in the transistor structure. Upon adsorption of molecules at the first side of the sensing film 40, an electrical property of the gate dielectric layer (sensing film 40) such as for example the work function or the fixed charge density changes, leading to a change in the conductivity of the transistor channel.

Figure 5:
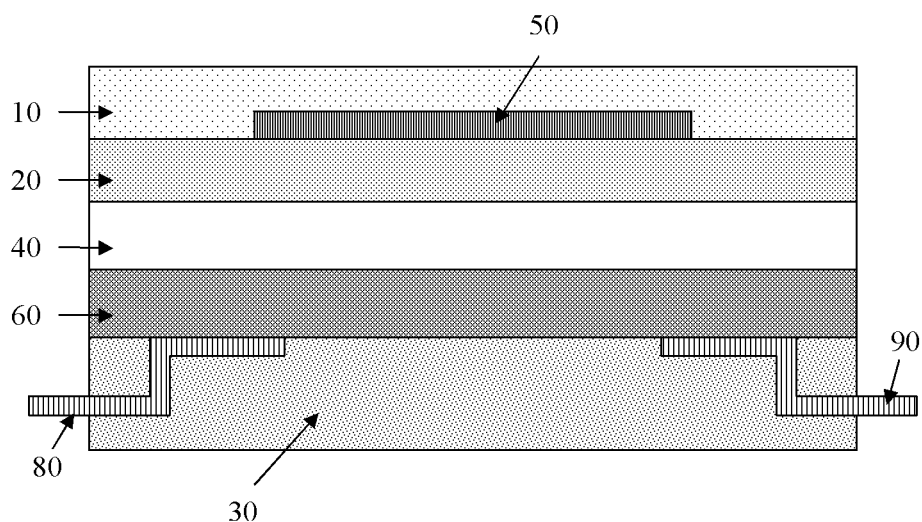
FIG. 5 shows a sensing device having a FET structure with a gap above a sensing layer having the function of gate dielectric layer.

FIG. 5 shows an embodiment of a sensing device comprising a thin sensing film 40, wherein the sensing device has a FET structure and wherein the sensing film 40 (insulating) forms the gate dielectric of the FET, there being a gap between the sensing film 40 and the field electrode 50 of the FET. In such a configuration, first medium 20 is the local environment comprising an analyte to be detected. Second medium 10 can for example be a dielectric support. The device comprises a first measurement electrode 80 and a second measurement electrode 90 in contact with the semiconductor layer 60, the electrodes having the function of a source electrode and a drain electrode in the transistor structure. Third medium 30 can for example be a dielectric substrate. Upon adsorption of molecules at a surface of the sensing film 40, the charge carrier density in the sensing film 40 changes, leading to a change in the conductivity of the transistor channel. Regeneration of the device can be obtained by applying a voltage pulse to the field electrode 50.

FIG. 6 shows an embodiment of a sensing device comprising a thin sensing film 40, wherein the sensing device has a TFT structure and wherein the sensing film 40 is a semiconducting film forming the channel of the transistor. The thin sensing film 40 is at a first side in contact with third medium 30, being the local environment, and at a second side opposite to the first side with first medium 20, being a dielectric medium 20. The sensing device comprises a field electrode 50 (gate electrode of the TFT) and two measurement electrodes 80, 90 (source and drain electrode of the TFT). Upon adsorption of molecules at the first side of the sensing film 40, the properties of the semiconducting thin sensing film 40 change. In particular, the work function and the charge carrier density change as a result of adsorption. It is not expected that work function changes alter the conductivity much because an electric potential that is much higher than the work function is generally needed to deplete the charge carrier density noticeably. The charge carrier density is modulated upon adsorption of molecules. An example of a mechanism is that oxygen atoms and other oxidative molecules are ionosorbed accepting a free electron from the sensing material (forming the channel of the transistor). As a result, oxidative molecules decrease the carrier density in the bulk of the sensing material. On the other hand, reductive molecules react with adsorbed oxygen and other oxidative molecules on the surface, which can result in donation of bound electrons to the bulk of the sensing material, thereby increasing the conductivity.

In this case, the charge carrier density in the TFT channel (sensing film 40) sets a limit on its thickness. Full depletion of the semiconducting thin sensing film would be needed, if a back gate influenced the surface properties, that is, the electro adsorptive effect played a role. The electric field, for which full depletion is achieved, is proportional to the area charge density. In a solid-state device the field electrode is separated by a dielectric from the semiconducting layer. For a reliable long-term operation of the device with an applied voltage, the reliability of the gate oxide is crucial. Therefore, the electric field in the gate oxide should not exceed the range of about 1-3 $MV \cdot cm^{-1}$ to avoid tunneling effects and field-induced degradation of the gate oxide. The charge carrier concentration in the sensing material can be in the order of about $10^{20}$ $cm^{-3}$. In one embodiment, it is required that the semiconducting thin sensing film has a thickness of less than about 10 nm to keep the area charge density and the electric field below the given limits.

The sensing structure shown in FIG. 6 can also represent a TFT structure wherein the sensing film 40 is at a second side in contact with the second medium 20, the second medium being the local environment. At a first side opposite to the second side, the sensing film 40 is in contact with a first measurement electrode 80 and a second measurement electrode 90. The third medium 30 can be a dielectric medium such as for example a dielectric substrate or a dielectric support. On a dielectric support 10 (second medium), a field electrode 50 is provided. Upon adsorption of molecules at the second side of the semiconducting sensing film 40, the properties of the sensing film change, e.g. the charge carrier density in the thin sensing film 40 changes and thus its conductivity changes.

When using continuous, ultrathin sensing films without grain boundaries according to one embodiment in a sensing device, low power consumption can be achieved as a result of the room temperature or ambient temperature operation that is enabled by the electro adsorptive effect. For example, a dielectric sensing film with a nanoscale thickness that is provided by ALD can reduce the voltages that are needed to reverse the molecular surface reactions with the electro adsorptive effect at room temperature or ambient temperature. A high sensitivity and a fast response can be obtained because of the high surface-to-volume ratio due to the nanoscale thickness of the thin sensing films. Planar film deposition and lithographic techniques allow for strong miniaturization and critical dimension control as well as for mass production. Integration with CMOS is possible in the back end of line (BEOL) of the fabrication process because low-temperature fabrication techniques such as chemical vapor deposition (CVD), atomic layer deposition (ALD) and rapid thermal annealing (RTA) at temperatures below 400° C. can be used to fabricate a sensing device comprising a thin sensing film according to one embodiment. SoC/SiP solutions using state-of-the-art semiconductor fabrication techniques are an advantageous way to integrate these heterogeneous functions in wireless, autonomous, transducer systems.

FIG. 9 schematically shows a sensing device with a structured substrate, resulting in an enhanced effective sensing area. Therein trenches are shown. In a similar manner pits may be formed. The trenches are covered with a first medium (20) and a sensing film (40). Also electrodes (80,90) are shown. Typical details of these elements are given above.

The foregoing description details certain embodiments of the invention. It will be appreciated, however, that no matter how detailed the foregoing appears in text, the invention may be practiced in many ways. It should be noted that the use of particular terminology when describing certain features or aspects of the invention should not be taken to imply that the terminology is being re-defined herein to be restricted to including any specific characteristics of the features or aspects of the invention with which that terminology is associated.

While the above detailed description has shown, described, and pointed out novel features of the invention as applied to various embodiments, it will be understood that various omissions, substitutions, and changes in the form and details of the device or process illustrated may be made by those skilled in the technology without departing from the spirit of the invention. The scope of the invention is indicated by the appended claims rather than by the foregoing description. All changes which come within the meaning and range of equivalency of the claims are to be embraced within their scope.

What is claimed is:
1. A method of sensing a predetermined analyte, the method comprising:

sensing a predetermined analyte with a sensing layer comprising an amorphous thin continuous film without grain boundaries, the sensing layer having a thickness in the range between about 1 nm and 100 nm, wherein sensing the predetermined analyte is performed at room temperature.

2. The method according to claim 1, wherein the sensing layer has a thickness in the range between about 1 nm and 30 nm.

3. The method according to claim 1, wherein the sensing layer is formed of one or more of the following: a polymer, an inorganic material, an oxide, a nitride, and a semiconductor, $SiO_2$, $Al_2O_3$, $HfO_2$, $Ta_2O_5$, $ZrO_2$, titanium oxide, iron oxide, manganese oxide, chromium oxide, cobalt oxide, nickel oxide, copper oxide, zinc oxide, tin oxide, molybdenum oxide, zirconium oxide, tungsten oxide, iridium oxide, an oxide of the lanthanide series, a noble metal catalyst particle, SiN, SiC, n-type or p-type doped silicon, a III-V binary, ternary and quaternary alloy, GaN, and a II-VI compound.

* * * * *